United States Patent
San et al.

(10) Patent No.: US 7,927,859 B2
(45) Date of Patent: Apr. 19, 2011

(54) HIGH MOLAR SUCCINATE YIELD BACTERIA BY INCREASING THE INTRACELLULAR NADH AVAILABILITY

(75) Inventors: Ka-Yiu San, Houston, TX (US); George N. Bennett, Houston, TX (US); Ailen Sánchez, Houston, TX (US)

(73) Assignee: Rice University, Houston, TX (US)

( * ) Notice: Subject to any disclaimer, the term of this patent is extended or adjusted under 35 U.S.C. 154(b) by 791 days.

(21) Appl. No.: 10/923,635

(22) Filed: Aug. 20, 2004

(65) Prior Publication Data

US 2005/0042736 A1 Feb. 24, 2005

Related U.S. Application Data (60) Provisional application No. 60/497,195, filed on Aug. 22, 2003.

(51) Int. Cl.
```
C12N 1/20       (2006.01)
C12N 9/02       (2006.01)
C12N 9/04       (2006.01)
C12N 9/10       (2006.01)
C12N 15/00      (2006.01)
C12P 7/64       (2006.01)
C12P 21/04      (2006.01)
C12Q 1/68       (2006.01)
C12Q 1/00       (2006.01)
C07H 21/04      (2006.01)
C07H 21/02      (2006.01)
```

(52) U.S. Cl. .................. 435/252.33; 435/189; 435/190; 435/440; 435/252.3; 435/320.1; 435/4; 435/6; 435/193; 435/135; 435/69.1; 536/23.2; 536/23.1

(58) Field of Classification Search .......................... None
See application file for complete search history.

(56) References Cited

U.S. PATENT DOCUMENTS

| | | | |
|---|---|---|---|
| 6,159,738 | A | 12/2000 | Donnelly et al. |
| 6,448,061 | B1 | 9/2002 | Pan et al. |
| 6,455,284 | B1 | 9/2002 | Gokarn et al. |
| 2003/0087381 | A1 | 5/2003 | Gokarn et al. |
| 2006/0040368 | A1 | 2/2006 | San et al. |
| 2006/0046288 | A1 | 3/2006 | Ka-Yiu et al. |
| 2006/0073577 | A1 | 4/2006 | Ka-Yiu et al. |
| 2006/0128001 | A1 | 6/2006 | Yukawa et al. |
| 2006/0141594 | A1 | 6/2006 | San et al. |

FOREIGN PATENT DOCUMENTS

| | | | |
|---|---|---|---|
| WO | WO 99/06532 | * | 2/1999 |
| WO | WO 2007/001982 | | 1/2007 |

OTHER PUBLICATIONS

Branden et al. Introduction to Protein Structure, Garland Publishing Inc., New York, p. 247, 1991.*
ExPASy—Formate Dehydrogenase.*
Vemuri et al. Effects of growth mode and pyruvate carboxylase on succinic acid production by metabolically engineered strains of *Escherichia coli*. Appl Environ Microbiol. Apr. 2002;68(4):1715-27.*
Goodbye et al. Cloning and sequence analysis of the fermentative alcohol-dehydrogenase-encoding gene of *Escherichia coli*. Gene. Dec. 21, 1989;85(1):209-14.*
Datsenko et al. One-step inactivation of chromosomal genes in *Escherichia coli* K-12 using PCR products. Proc Natl Acad Sci U S A. Jun. 6, 2000;97(12):6640-5.*
Berrios-Rivera et al. Metabolic engineering of *Escherichia coli*: increase of NADH availability by overexpressing an NAD(+)-dependent formate dehydrogenase. Metab Eng. Jul. 2002;4(3):217-29.*
Gupta et al. *Escherichia coli* derivatives lacking both alcohol dehydrogenase and phosphotransacetylase grow anaerobically by lactate fermentation. J Bacteriol. Jul. 1989;171(7):3650-5.*
Alam, K et al., Anaerobic fermentation balance of *E. coli* as observed by in vivo nuclear magnetic resonance spectroscopy; J. of Bacteriology, vol. 171(11), pp. 6213-7, Nov. 1989.
Aristidou AA, San Ky, Bennett GN. Metabolic engineering of *Escherichia coli* to enhance recombinant protein production through acetate reduction. Biotechnol Prog. Jul.-Aug. 1995;11(4):475-8.
Aristidou AA, San Ky, Bennett GN. Metabolic flux analysis of *Escherichia coli* expressing the *Bacillus subtilis* acetolactate synthase in batch and continuous cultures. Biotechnol Bioeng. Jun. 20, 1999;63(6):737-49.
Gokarn, R. R.; Eiteman, M. A.; Altman, E. Expression of pyruvate carboxylase enhances succinate production in *Escherichia coli* without affecting glucose uptake rate. Biotech. Let. 1998, 20, 795-798.
U.S. Appl. No. 10/923,635, filed Aug. 20, 2004, San et al.
U.S. Appl. No. 10/987,511, filed Nov. 12, 2004, San et al.
U.S. Appl. No. 10/286,326, filed Nov. 2, 2002, San et al.
U.S. Appl. No. 60/604,922, filed Aug. 27, 2004, San et al.
U.S. Appl. No. 60/599,956, filed Aug. 9, 2004, San et al.
U.S. Appl. No. 60/610,750, filed Sep. 17, 2004, San et al.
U.S. Appl. No. 60/638,765, filed Dec. 22, 2004, San et al.
Gokarn, R. R.; Eiteman, M. A.; Altman, E. Metabolic analysis of *Escherichia coli* in the presence and absense of the carboxylating enzymes phosphoenolpyruvate carboxylase and pyruvate carboxylase. Appl Environ Microbiol. 2000, 666, 1844-1850.

(Continued)

Primary Examiner — Yong D Pak
(74) Attorney, Agent, or Firm — Boulware & Valoir (57) ABSTRACT

The invention relates to increasing the yield of succinate in bacteria by increasing the intracellular availability of cofactors such as NADH.

18 Claims, 4 Drawing Sheets

OTHER PUBLICATIONS

Hahm, D. H.; Pan, J. G.; Rhee, J. S. Characterization and evaluation of a pta (phosphotransacetylase) negative mutant of *Escherichia coli* HZB101 as a production host of foreign lipase. Appl Microbiol Biotechnol. 1994, 42, 100-107.

Holms, W. H. The central metabolic pathways in *Escherichia coli*: relationship between flux and control at a branchpoint, efficiency of conversion to biomass, and excretion of acetate. Curr Top Cell Regul. 1986, 28, 69-105.

Hong, S. H.; Lee, S.-Y. Importance of redox balance on the production of succinic acid by metabolically engineered *Escherichia coli*. Appl Microbiol Biotechnol. 2002, 58, 286-290.

Leonardo, M. et al., Anaerobic regulation of the adhE gene, encoding the fermentative alcohol dehydrogenase of *E. coli*; J. of Bacteriology, vol. 175(3), pp. 870-8, Feb. 1993.

Levanon SS, San KY, Bennett GN. Effect of oxygen on the *Escherichia coli* ArcA and FNR regulation systems and metabolic responses.Biotechnol Bioeng. Mar. 5, 2005;89(5):556-64.

Lin H, San KY, Bennett GN. Effect of Sorghum vulgare phosphoenolpyruvate carboxylase and *Lactococcus lactis* pyruvate carboxylase coexpression on succinate production in mutant strains of *Escherichia coli*.Appl Microbiol Biotechnol. Nov. 24, 2004; [Epub ahead of print].

Lin H, Vadali RV, Bennett GN, San KY. Increasing the acetyl-CoA pool in the presence of overexpressed phosphoenolpyruvate carboxylase or pyruvate carboxylase enhances succinate production in *Escherichia coli*. Biotechnol Prog. Sep.-Oct. 2004;20(5):1599-604.

Luli, G. W.; Strohl, W. R. Comparison of growth, acetate production, and acetate inhibition of *Escherichia coli* strains in batch and fed-batch fermentations. Applied and Environmental Microbiology. 1990, 56, 1004-1011.

Park, D. et al., Utilization of electrically reduced neutral red by *Actinobacillus succinogenes*: physiological functio of neutral red in membrane-driven fumarate reduction and energy conservation; J. of Bacteriology, vol. 181(8), pp. 2403-2410, Apr. 1999.

Phillips, G. J.; Park, S. K.; Huber, D. High copy number plasmids compatible with commonly used cloning vectors. Biotechniques. 2000, 28, 400-408.

San KY, Bennett GN, Berrios-Rivera SJ, Vadali RV, Yang YT, Horton E, Rudolph FB, Sariyar B, Blackwood K. Metabolic engineering through cofactor manipulation and its effects on metabolic flux redistribution in *Escherichia coli*. Metab Eng. Apr. 2002;4(2):182-92.

Sanchez, A. M.; Bennett, G. N.; San, K.-Y. Efficient succinate production from glucose through overexpression of pyruvate carboxylase in an *Escherichia coli* alcohol dehydrogense and lactate dehydrogenase mutant. Submitted. 2004a.

Vemuri, G. N.; Eiteman, M. A.; Altman, E. Effect of growth mode and pyruvate carboxylase on succinic acid production by metabolically engineered strains of *Escherichia coli*. Appl Environ Microbiol. 2002, 68, 1715-1727.

Yang YT, Aristidou AA, San KY, Bennett GN. Metabolic flux analysis of *Escherichia coli* deficient in the acetate production pathway and expressing the *Bacillus subtilis* acetolactate synthase. Metab Eng. Jan. 1999;1(1):26-34.

Yang YT, Bennett GN, San KY. Effect of inactivation of nuo and ackA-pta on redistribution of metabolic fluxes in *Escherichia coli*. Biotechnol Bioeng. Nov. 5, 1999;65(3):291-7.

Yang YT, Bennett GN, San KY. The effects of feed and intracellular pyruvate levels on the redistribution of metabolic fluxes in *Escherichia coli*. Metab Eng. Apr. 2001;3(2):115-23.

Yang YT, Peredelchuk M, Bennett GN, San KY. Effect of variation of *Klebsiella pneumoniae* acetolactate synthase expression on metabolic flux redistribution in *Escherichia coli*. Biotechnol Bioeng. Jul. 20, 2000;69(2):150-9.

San, Ka-Yiu et al., *Metabolic Engineering through Cofactor Manipulation and its Effects on Metabolic Flux Redistribution in Escherichia coli*, Metabolic Engineering 4, pp. 182-192,(2002).

\* cited by examiner

HIGH MOLAR SUCCINATE YIELD BACTERIA BY INCREASING THE INTRACELLULAR NADH AVAILABILITY

PRIOR RELATED APPLICATIONS

This application claims the benefit of U.S. Provisional Application No. 60/497,195, filed Aug. 22, 2003.

FEDERALLY SPONSORED RESEARCH STATEMENT

The present invention has been developed with funds from the National Science Foundation. Therefore, the United States Government may have certain rights in the invention.

REFERENCE TO MICROFICHE APPENDIX

Not applicable.

FIELD OF THE INVENTION

The invention relates to increasing the yield of succinate in bacteria by increasing the intracellular availability of cofactors such as NADH.

BACKGROUND OF THE INVENTION

Succinic acid has drawn much interest because it has been used as a precursor of numerous chemicals including pharmaceuticals and biodegradable polymers. Succinic acid is a member of the $C_4$-dicarboxylic acid family and it is commercially manufactured by hydrogenation of maleic anhydride to succinic anhydride, followed by hydration to succinic acid. Recently major efforts have been made to produce succinic acid by microbial fermentation using a renewable feedstock. Many attempts have been made to metabolically engineer the anaerobic central metabolic pathway of *Escherichia coli* (*E. coli*) to increase succinate yield and productivity. *E. coli* is extensively used in industry as a host for many products due to the ease of genetic manipulation coupled to its fast growth rate, standardized cultivation techniques and cheap media. It is for this reason and for the need to produce succinic acid economically at high concentrations and yields that *E. coli* has been considered as a potential candidate to produce this product of industrial interest.

It is well known that under anaerobic conditions and in the absence of exogenous electron acceptors, *E. coli* metabolizes glucose to a mixture of fermentative products consisting primarily of acetate, ethanol, lactate and formate with smaller quantities of succinate. NADH produced by the catabolism of glucose is regenerated to NAD+ through the reduction of intermediate metabolites derived from glucose in order to continue with glycolysis. The distribution of products varies according to the strain and growth conditions and is dictated by the way reducing equivalents generated in the form of NADH are consumed so that an appropriate redox balance is achieved by the cell.

Numerous efforts have been undertaken to make succinate the major fermentation product in *E. coli*. Some genetic manipulations previously studied are: deletion of the fermentative lactate dehydrogenase (LDH) pathway, deletion of both the LDH and pyruvate formate lyase (PFL) pathways and deletion of multiple pathways including PFL and LDH pathways with an additional ptsG mutation which restored the ability of the strain to grow fermentatively on glucose and resulted in increased production of succinic acid. Other studies include overexpression of phosphoenolpyruvate carboxylase, (PEPC), overexpression of the malic enzyme and overexpression of pyruvate carboxylase (PYC). Besides these genetic manipulations, external means have been developed in order to increase succinate production such as utilizing a dual phase fermentation production mode which comprises an initial aerobic growth phase followed by an anaerobic production phase, or by changing the headspace conditions of the anaerobic fermentation using carbon dioxide or hydrogen. It has been suggested that an external supply of $H_2$ might serve as a potential electron donor for the formation of succinic acid, a highly reduced fermentation product when compared to glucose.

Under fully anaerobic conditions, the maximum theoretical yield (molar basis) of succinate from glucose is one based on the number of reducing equivalents provided by this substrate. One mole of glucose can provide only two moles of NADH, and two moles of NADH can only produce one mole of succinate, therefore, in order to surpass the maximum theoretical yield it is necessary to use part of the carbon coming from glucose to provide additional reducing power to the system.

Metabolic engineering has the potential to considerably improve process productivity by manipulating the throughput of metabolic pathways. Specifically, manipulating intermediate substrate levels can result in greater than theoretical yields of a desired product.

SUMMARY OF THE INVENTION

An aspect of the invention is directed toward a method of increasing the production of succinate within a cell by mutating one or more genes that encode enzymes involved in metabolic reactions, and the mutations result in increased intracellular levels of NADH.

Another aspect of the invention is directed toward a method of increasing the NADH flux in a cell, by mutating one or more genes that encode enzymes involved in metabolic reactions, and the mutations result in increased intracellular levels of NADH.

A further aspect of the invention is directed toward a microorganism which contains one or more mutant genes, and displays increased intracellular levels of NADH.

BRIEF DESCRIPTION OF THE DRAWINGS

The accompanying drawings which are incorporated in and constitute a part of this specification exemplify the invention and together with the description, serve to explain the principles of the invention.

DESCRIPTION OF EXEMPLARY EMBODIMENTS

An embodiment of the invention is directed towards an *E. coli* strain that is capable of achieving high succinate yield and productivity by diverting maximum quantities of NADH for succinate synthesis by striking a balance between cell physiology requirements and achieving higher product yields.

An embodiment of the invention provides a strain of *E. coli* in which both the ethanol and lactate synthesis pathways are inactivated by mutating the genes that code for the enzymes involved in these pathways namely lactate dehydrogenase (LDH) and alcohol dehydrogenase (ADH; AdhE). The AdhE protein of *E. coli* is responsible for three different enzymatic functions. The ADH and coenzyme A-linked acetaldehyde dehydrogenase (ACDH) functions are involved in the conversion of acetyl-CoA to ethanol during fermentation. Therefore, mutation of the adh gene entirely inactivates the ethanol synthesis pathway of the respective mutant strain.

An embodiment of the invention provides a double mutant strain of *E. coli* in which the ldh and adh genes are inactivated and the mutant strain is transformed with a plasmid expressing an NAD-dependent formate dehydrogenase capable of NADH recycling.

In certain embodiments of the invention, the dual mutant *E. coli* strain containing the plasmid expressing an NAD-dependent formate dehydrogenase is further transformed with a plasmid expressing the pyruvate carboxylase gene.

In an embodiment of the invention, the pyruvate carboxylase gene is derived from *Lactococcus lactis*.

In other embodiments of the invention, the glucose permease in the phosphotransferase (ptsG) system of the *E. coli* double mutant is additionally mutated. This triple mutant is able to further increase the molar succinate yield.

In certain embodiments of the invention, the native formate dehydrogenase gene (fdhf) is additionally mutated to generate a triple mutant.

In an embodiment of the invention, an *E. coli* strain that contains mutations in the adhE, ldh and ptsG genes is transformed with a plasmid expressing the gene encoding pyruvate carboxylase. In an embodiment of the invention, the pyruvate carboxylase gene is derived from *Lactococcus lactis*.

In certain embodiments of the invention, an *E. coli* strain that contains mutations in the adhE, ldh and fdhf genes is transformed with a plasmid expressing the gene encoding pyruvate carboxylase. In an embodiment of the invention, the pyruvate carboxylase gene is derived from *Lactococcus lactis*.

In certain embodiments of the invention, increased succinate yields are achieved by the increased conversion of pyruvate to oxaloacetate by overexpressing phosphoenolpyruvate carboxylase (PEPC) and/or pyruvate carboxylase (PYC).

In other embodiments of the invention, increased succinate yields are achieved via reduced glucose uptake rate by using glucose uptake deficient strains, such as a mutated ptsG system.

In certain embodiments of the invention, increased succinate yields are achieved via increased pyruvate to acetyl-CoA flux to increase NADH supply by overexpressing an oxidoreductase enzyme system or pyruvate formate lyase (PFL).

In other embodiments of the invention, the rate of succinate formation can be further improved by using a dual phase process where the growth and the production phase of the culture are operated in a sequential manner.

An embodiment of the invention is directed toward a microorganism that contains one or more mutant genes and displays increased yields of succinate.

Another embodiment of the invention is directed toward a microorganism that displays a molar ratio of succinate yield to glucose substrate of greater than 1.0.

A further embodiment of the invention is directed toward a microorganism that displays a molar ratio of succinate yield to glucose substrate that is at least about 1.3.

Another aspect of the invention is directed toward a microorganism that displays a molar ratio of succinate yield to glucose substrate that is greater than about 1.3.

Figure 1:
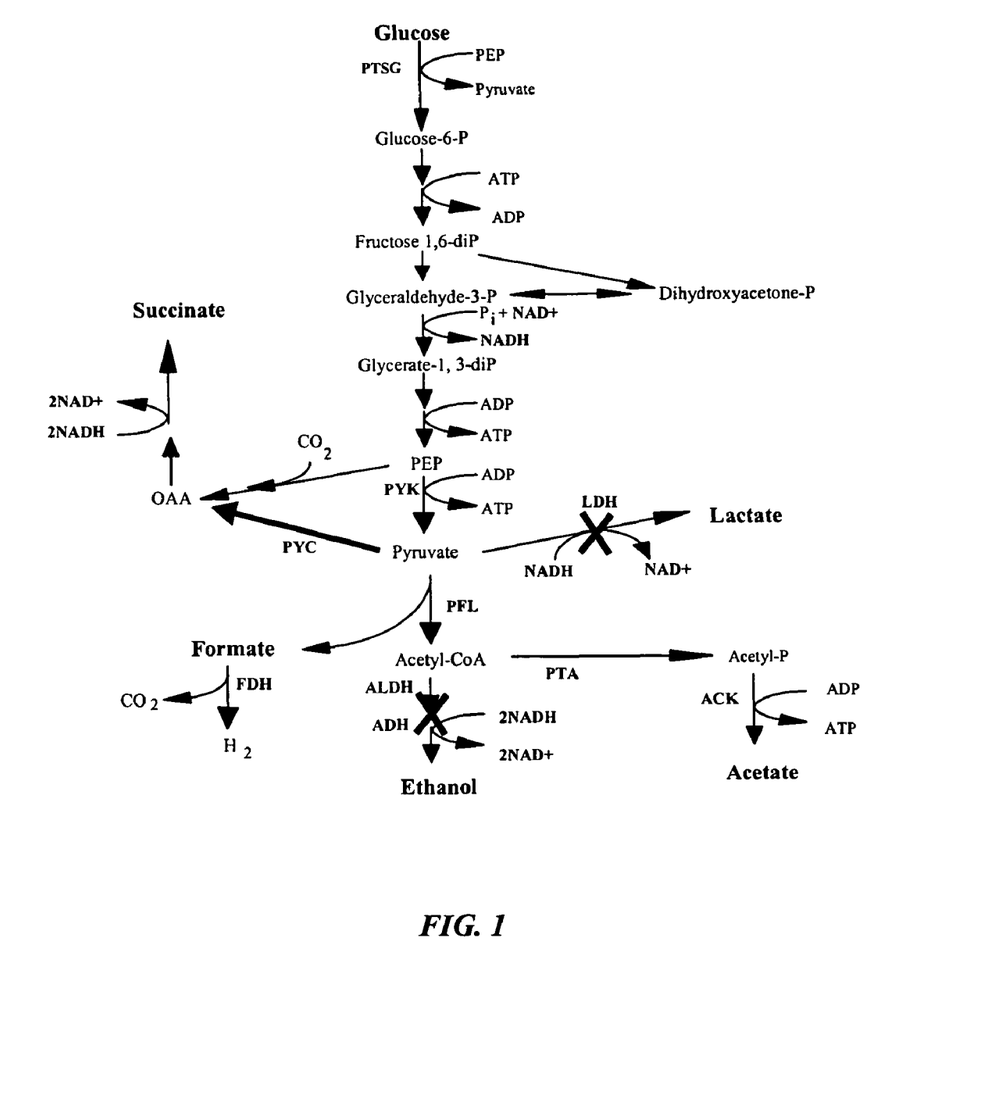
FIG. 1 illustrates the central anaerobic metabolic pathway of the strain SBS110MG showing inactivation of lactate dehydrogenase and alcohol dehydrogenase pathways, and overexpression of a plasmid that expresses pyruvate carboxylase from *Lactococcus lactis*.
Figure 2:
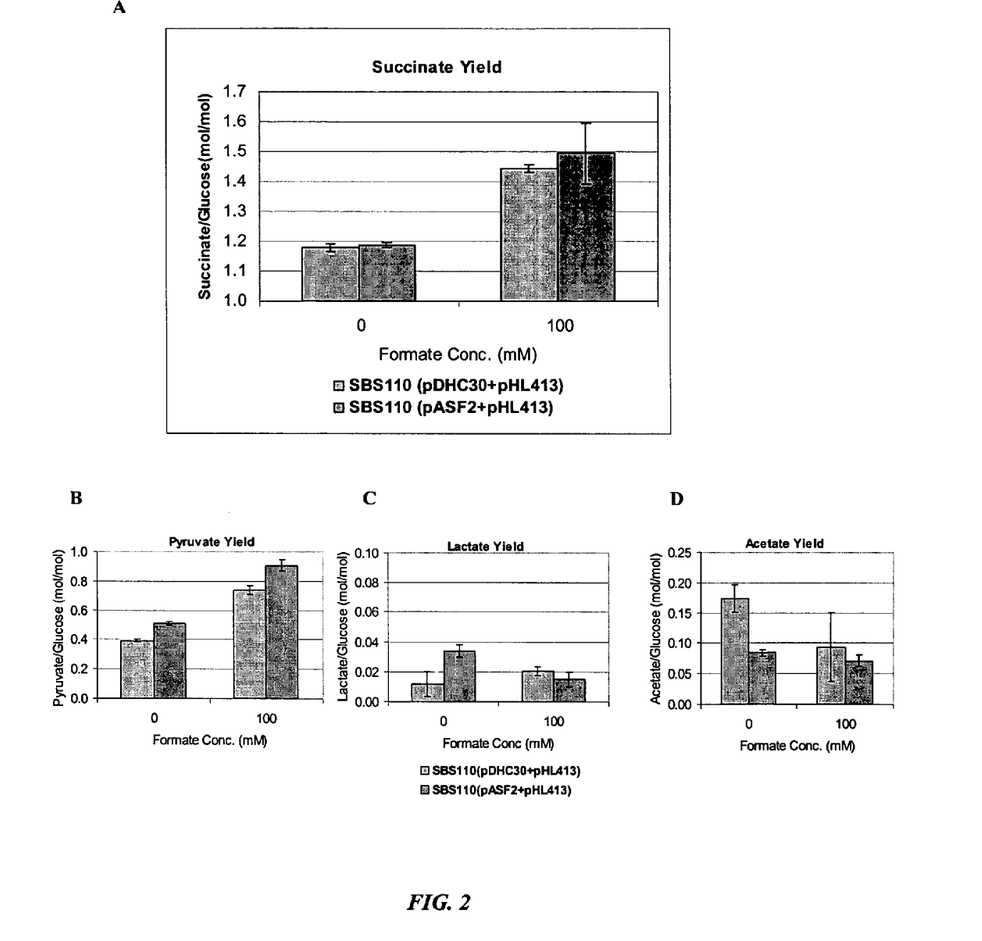
FIG. 2 illustrates the effect of formate supplementation (A) on succinate yield and other metabolites (pyruvate (B); lactate (C); acetate (D)) in the SBS110P strain that is transformed with a plasmid that expresses NAD-dependent formate dehydrogenase along with a plasmid that expresses pyruvate carboxylase, and the strain SBS110(pHL413) containing a plasmid that expresses pyruvate carboxylase and a control plasmid pDHC30.

Referring to FIG. 1, the central anaerobic metabolic pathway of the strain SBS110MG showing inactivation of lactate dehydrogenase and alcohol dehydrogenase pathways, and overexpression of a plasmid that expresses pyruvate carboxylase from *Lactococcus lactis* is depicted. The AdhE protein of *E. coli* is responsible for three different enzymatic activities. Two of these activities, ADH and coenzyme A-linked acetaldehyde dehydrogenase (ACDH), are involved in the conversion of acetyl-CoA to ethanol during fermentation Referring to FIG. 2, two enzymes in the central anaerobic pathway, lactate dehydrogenase (LDH) and alcohol dehydrogenase (ADH; AdhE) were deactivated to generate the mutant strain SBS110. A test mutant strain was created by transforming the dual mutant strain with two plasmids, one expressing NAD-dependent formate dehydrogenase (pASF2), and the other expressing pyruvate carboxylase (pHL413). Control experiments were performed with the dual mutant strain transformed with a plasmid expressing pyruvate carboxylase (pHL413) and a control plasmid (pDHC30). The molar succinate yield for the test mutant strain was higher (1.5 mol/mol) than the control strain.

Figure 3:
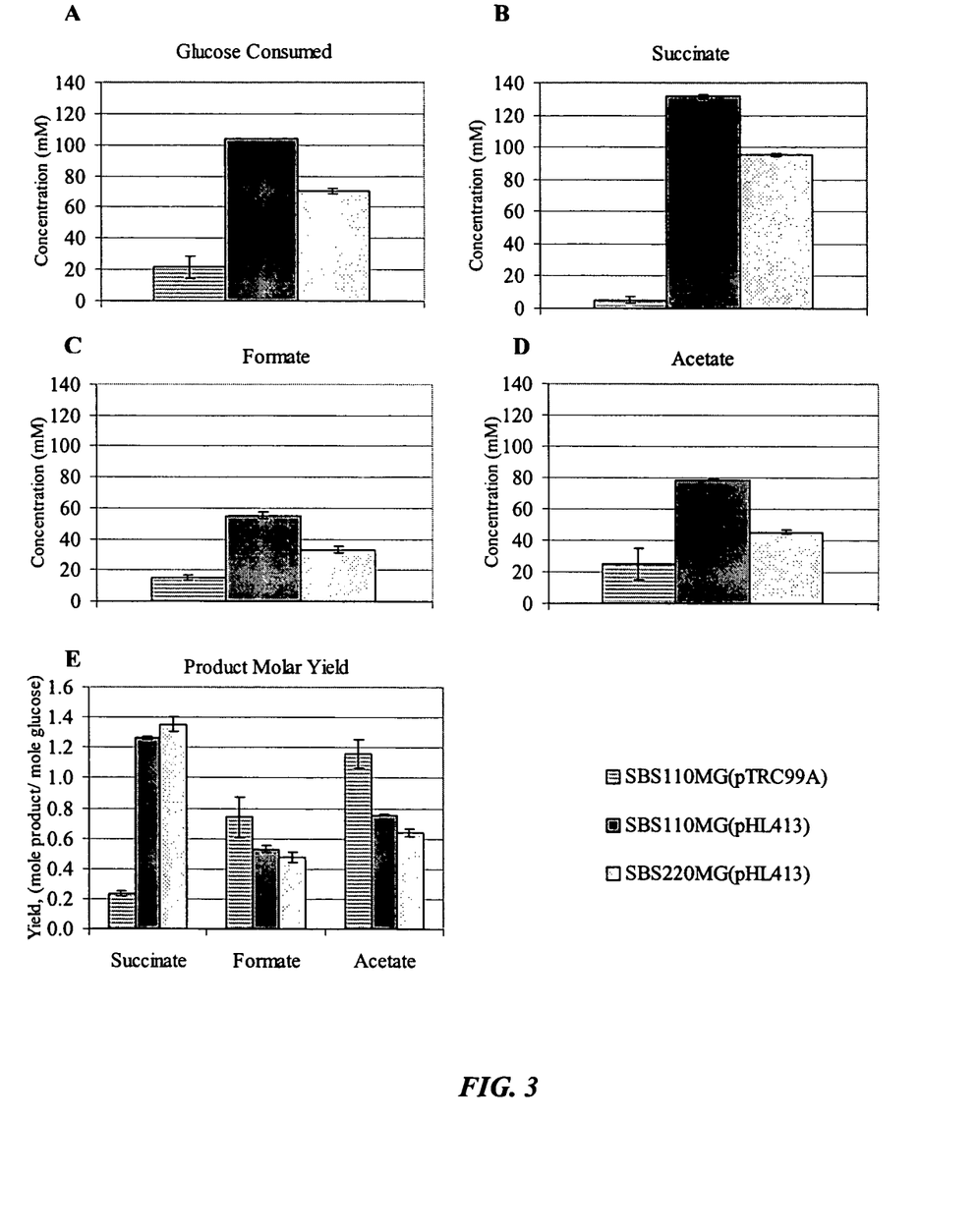
FIG. 3 illustrates metabolite concentrations (mM) and product yields (succinate (B); formate (C); acetate (D); product molar yield (E)) in anaerobic experiments using glucose as a carbon source (A) in Luria Broth medium with a starting OD of 20. Concentrations shown are from samples collected after 48 hours of culture (average of triplicate cultures). The error bars represent the standard deviation.

FIG. 3 illustrates the metabolite concentrations and product yields in two mutant strains, a double mutant (ΔadhEΔldhA) and a triple mutant (ΔadhEΔldhAΔptsG) transformed with a plasmid that expresses pyruvate carboxylase (pHL413). The experimental details and results are detailed below.

Figure 4:
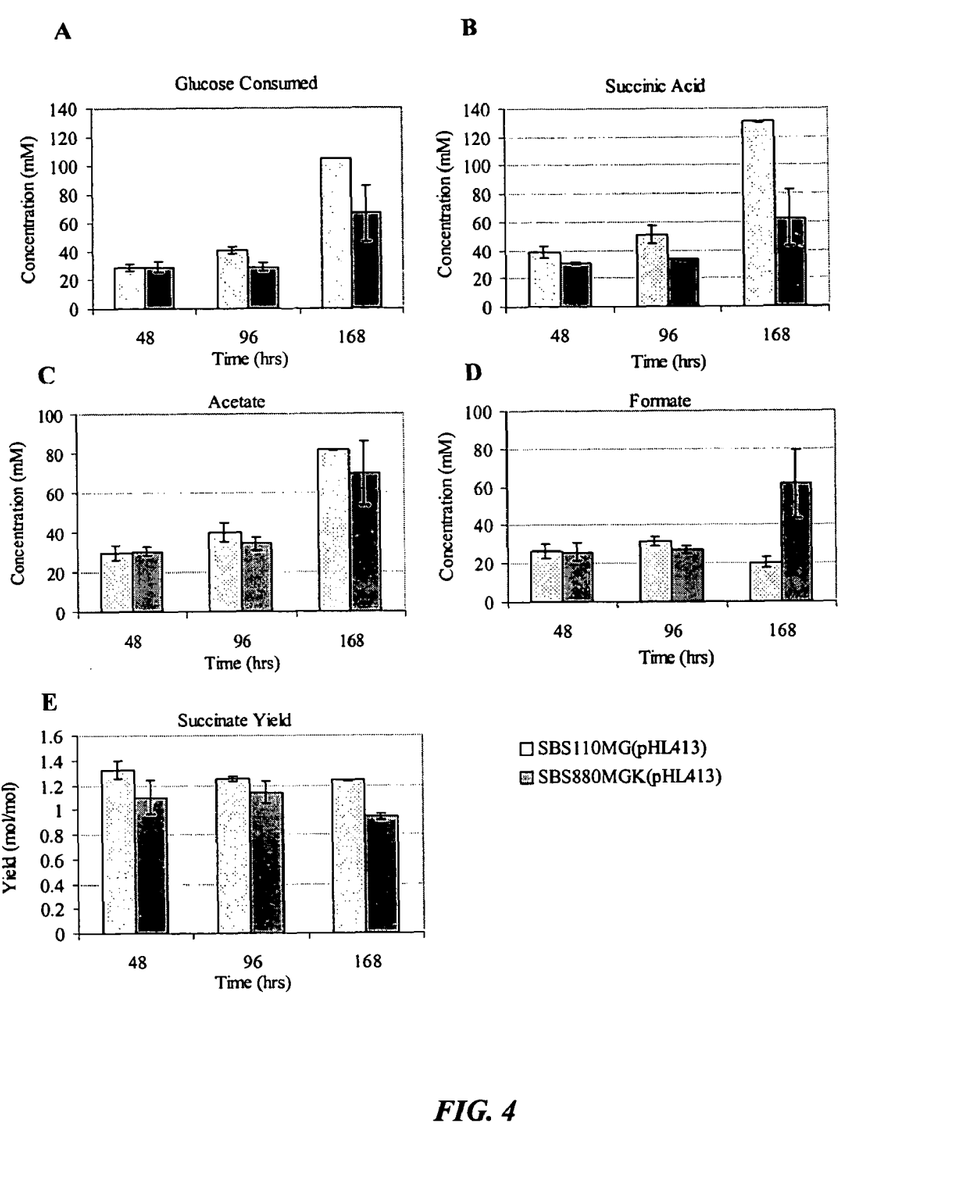
FIG. 4 illustrates metabolite concentrations (mM) and product yields (succinate (B); formate (C); acetate (D); succinate molar yield (E)) in anaerobic experiments using glucose as a carbon source (A) on LB medium with a starting OD of 4. Concentrations shown are from samples collected after 48, 96 and 168 hours of culture (average of triplicate cultures). The error bars represent the standard deviation.

FIG. 4 illustrates the metabolite concentrations and product yields in two triple mutant strains, SBS220MG (ΔadhEΔldhAΔptsG) and SBS880MG (ΔadhEΔldhAΔfdhF) transformed with a plasmid that expresses pyruvate carboxylase (pHL413). The experimental details and results are detailed below.

Example 1

Construction of Plasmids and Mutant Strains

Table 1 describes the strains used in this study and Table 2 describes the plasmids used in this study. Single mutations were performed individually on MG1655 using the λ Red recombinase method of chromosomal disruption. Additional mutations were introduced by P 1-phage transduction with subsequent elimination of the kanamycin resistance gene. Single gene disruption sites were verified by PCR. Plasmid pHL413 contains the pyc gene from *Lactococcus lactis*, which encodes the enzyme pyruvate carboxylase that converts pyruvate to oxaloacetate.

TABLE 1

| Strain | Phenotype |
|---|---|
| MG1655 | Wild type ($F^-\lambda^-$) |
| SBS110 | $\Delta adhE \Delta ldhA$ |
| SBS110MG | $\Delta adhE \Delta ldhA$, $Km^S$ |
| SBS220MG | $\Delta adhE \Delta ldhA \Delta ptsG$, $Km^S$ |
| SBS880MGK | $\Delta adhE \Delta ldhA \Delta fdhF$, $Km^R$ |
| SBS100MG | $\Delta adhE$, $Km^S$ |
| CD55K | $\Delta ldhA$, $Km^R$ |
| SBS770MG | $\Delta fdhF$, $Km^R$ |
| BW25113 | $\Delta ptsG$, $Km^R$ |

TABLE 2

| Plasmid | Properties |
|---|---|
| pHL413 | Pyruvate carboxylase from *Lactococcus lactis* cloned in pTrc99A, $Ap^R$ |
| pASF2 | NAD-dependent formate dehydrogenase expression plasmid |
| pTrc99A | Control plasmid |
| pDHC30 | Control plasmid |

Example 2

Culture of Bacterial Strain

Luria-Bertani (LB) broth medium supplemented with 200 mg/L of 1:1:1 ampicillin, carbenicillin and oxacillin was used for all aerobic cultivations. LB broth medium supplemented with 20 g/L of glucose and 1 g/L of $NaHCO_3$ was used for all anaerobic cultivations and ampicillin was added at a concentration of 200 mg/L. Pyruvate carboxylase expression was induced by the addition of isopropyl-β-D-thiogalactopyranoside (IPTG) to a final concentration of 1 mM.

A two-stage culture technique was used to examine the accumulation of succinic acid in the culture broth. The first stage comprises an initial aerobic growth phase followed by the second stage, the anaerobic production phase. Cells were grown aerobically in LB broth containing appropriate antibiotic concentration at 37° C. and 250 rpm for 17 hours. Cells were harvested by centrifugation and the supernatant discarded. Then the cells were resuspended in fermentation medium at two different cell densities of 4 or 20 OD units respectively. After resuspension, the cultures were transferred aseptically to anaerobic culture containers, which contained $MgCO_3$. The containers were purged with $CO_2$ at 1 L/min at STP.

For low inoculum experiments, triplicate cultures were grown aerobically using 125-ml shake flasks containing 25 ml of LB medium with appropriate antibiotic concentration. A volume of this culture was centrifuged, and the cells collected were resuspended in 18 ml of anaerobic medium to an initial OD of 4. The cells were transferred aseptically to 45 ml glass anaerobic tubes containing 0.5 g of $MgCO_3$. The resuspended culture was purged with sterile $CO_2$ at 1 L/min STP for 8 seconds and rapidly capped with open top caps and PTFE/silicone rubber septa to ensure anaerobic conditions. A sample of the initial media was saved for analysis and samples were withdrawn with a syringe at 48, 96 and 168 h.

For higher inoculum experiments, aerobic cultures were grown in a 2 L shake flask containing 400 ml of LB medium with appropriate antibiotic concentration. A volume of this culture was centrifuged, and the cells collected were resuspended in 10 ml of anaerobic medium to an initial OD of 20. The cells were transferred aseptically to 250 ml shake flasks containing 0.5 g of $MgCO_3$. The resuspended culture was purged with sterile $CO_2$ at 1 L/min STP for 1 min and rapidly capped with rubber stoppers to ensure anaerobic conditions. For higher inoculum experiments, the use of shake flasks allowed a larger $CO_2$/liquid ratio avoiding $CO_2$ limitation conditions. A sample of the initial media was saved for analysis and samples were withdrawn with a syringe at 24 and 48 h.

Example 3

Analytical Techniques

Cell density was measured at 600 nm in a spectrophotometer. Fermentation samples were centrifuged for 3 min at 13,000 g in a microcentrifuge. The supernatant was filtered through a 0.45 μm syringe filter and stored chilled for HPLC analysis. The fermentation products as well as glucose were quantified using a Shimadzu HPLC system, equipped with a cation-exchanged column, a UV detector and a differential refractive index detector. A mobile phase of 2.5 mM $H_2SO_4$ solution at a 0.6 ml/min flow rate was used and the column was operated at 55° C.

Example 4

Effects of Overexpression of Pyruvate Carboxylase

Experiments were performed with strain SBS110 transformed with a plasmid expressing formate dehydrogenase along with a plasmid expressing pyruvate carboxylase. As shown in Table 3 and FIG. 2, an increased yield of succinate is observed when the strain is grown in the presence of added formate.

TABLE 3

| | Formate added | |
|---|---|---|
| Metabolite yield | 0 mM | 100 mM |
| Succinate Yield | | |
| SBS110(pDHC30 + pHL413) | 1.18 | 1.44 |
| SBS110(pASF2 + pHL413) | 1.19 | 1.49 |
| Pyruvate Yield | | |
| SBS110(pDHC30 + pHL413) | 0.39 | 0.74 |
| SBS110(pASF2 + pHL413) | 0.51 | 0.91 |
| Acetate Yield | | |
| SBS110(pDHC30 + pHL413) | 0.17 | 0.09 |
| SBS110(pASF2 + pHL413) | 0.08 | 0.07 |
| Lactate Yield | | |
| SBS110(pDHC30 + pHL413) | 0.01 | 0.02 |
| SBS110(pASF2 + pHL413) | 0.03 | 0.02 |
| Ethanol | | |
| SBS110(pDHC30 + pHL413) | BDL | BDL |
| SBS110(pASF2 + pHL413) | BDL | BDL |

BDL: below detection level

Anaerobic tube experiments were performed under a complete atmosphere of $CO_2$ using an initial OD of 4 with strain SBS110MG with and without plasmid pHL413 to assess the effect of overexpressing the pyc gene. Samples taken at different time intervals (48, 96 and 168 hrs) indicated that the expression of the pyc gene (plasmid pHL413) was necessary to increase the glucose uptake and to obtain high succinate yields. Fermentations with SBS110MG(pTrc99A) and SBS110MG(pHL413) were terminated after 168 h. At this point the control strain consumed only 11% of the initial glucose added (20 g/L) with low succinate yield and high acetate yield while SBS110MG(pHL413) consumed 100% of the initial glucose achieving a succinate yield of 1.3 mol/mol.

The effect of inoculum size on succinate production was also examined by using a higher inoculum of 20 OD units. FIG. 3 shows the results of these experiments, including glucose consumed, the concentration of the metabolites produced and the product yields after 48 h of culture.

A comparison of the results for SBS110MG (pTrc99A) and SBS110MG(pHL413) shows the effect of overexpressing pyc on the metabolic patterns of SBS110MG (FIG. 3). The glucose consumption increased 4 fold; the succinate increased 25 fold from 5 mM to 132 mM from an initial glucose concentration of 104 mM. As expected, overexpression of pyc increased the succinate yield from 0.2 mol/mol to 1.3 mol/mol, while the acetate yield dropped from 1.2 mol/mol to 0.8 mol/mol. The residual formate yield was also lower in the strain overexpressing pyc relative to the control strain. The residual formate dropped from 0.7 mol/mol to 0.5 mol/mol.

Example 5

Effects of Deletion of Formate Dehydrogenase

To investigate the effect of eliminating the fdhF gene, which encodes the native formate dehydrogenase (FDH) FDH-H, subunit of the formate hydrogen lyase (FHL) complex that converts formate to $CO_2$ and $H_2$, strain SBS880MGK was constructed by eliminating the native fdhF gene from SBS110MG, both strains were transformed with pHL413 and anaerobic tube experiments were performed.

FIG. 4 shows the results obtained in anaerobic tube experiments performed using an initial OD of 4. The cultures were analyzed after different time intervals (48, 96 and 168 h). A comparison of the results for the strain SBS110MG(pHL413) with SBS880MGK(pHL413) indicates the effect of eliminating the native FDH on the metabolic pattern of SBS110MG (pHL413). As can be seen from FIG. 4, no significant differences were observed for the first 48 h of culture between both strains in glucose consumption, succinate, acetate, residual formate levels or succinate yield. After 96 h significant differences in glucose consumption and succinate levels were noticed but no apparent change in the succinate yield was observed. After 168 h a decrease in residual formate yield was observed for SBS110MG(pHL413) relative to 48 h, while the residual formate yield remain constant for the strain lacking FDH activity. Glucose consumption, succinate levels and yield were significantly lower at this time interval. The acetate levels were similar, however the acetate yield was found to be higher for the fdhF⁻ strain. Strain SBS110MG (pHL413) consumed 100% of the glucose after 168 h while SBS880MGK(pHL413) consumed 62% of the initial glucose. SBS110MG(pHL413) was able to sustain the succinate molar yield in the range of 1.2 to 1.3 through the entire fermentation period, while the succinate yield of SBS880MGK(pHL413) dropped to 0.9 mol/mol by the end of the fermentation process.

After 48 hours of culture, succinate, residual formate or acetate yield were similar in strains SBS110MG(pHL413) and SBS880MGK(pHL413). After 96 h, acetate and residual formate yields decrease for SBS110MG(pHL413) relative to SBS880MGK(pHL413), however the succinate yield was not significantly different. After 168 h, the residual formate and acetate yield of SBS110MG(pHL413) decreases abruptly to 0.19 and 0.8 respectively with concomitant increase in glucose consumption and succinate levels (see FIG. 4) in contrast to the strain lacking the native FDH. As expected the residual formate yield remained unchanged after each time interval analyzed with the fdhF⁻ strain.

Example 6

Effect of PTSG Deletion

It has been shown that when a mutation of the ptsG was introduced into *E. coli* strains that could ferment glucose, the resulting strain was able to produce more succinate and less acetate. Based on these findings and to evaluate the possibility of a further increase in succinate yield and a decrease in acetate we transferred the ptsG mutation into strain SBS110MG to create SBS220MG. The triple mutant was transformed with plasmid pHL413 and experiments were performed under anaerobic conditions using a high cell density inoculum. The results of these experiments are depicted in FIG. 3, including glucose consumed (mM) and the concentration of different metabolites produced (mM) after 48 h of culture. Pyruvate, lactate and ethanol concentrations were not detected. Inactivation of the ptsG system significantly decreased the glucose consumed, while increasing the succinate yield and reducing the acetate yield as expected. The percent increase/decrease in product yields of the ptsG⁻ strain relative to the double mutant strain SBS110MG(pHL413) was a 7% increase in succinate yield and a 15% decrease in acetate yield. The results presented in FIG. 3 are the cultures analyzed after 48 h, but additional runs performed with strain SBS110MG(pHL413) revealed that 100% of the initial glucose could be consumed in 24 h. These results indicate that the presence of the ptsG mutation slows down the glucose consumption rate, therefore favoring succinate generation and reducing the amount of acetate wasted.

What is claimed is:

1. An engineered *Escherichia coli* (*E. coli*), said *E. coli* comprising a DNA that expresses pyruvate carboxylase (pyc), further comprising inactivated *E. coli* genes encoding alcohol dehydrogenase (adh) and lactate dehydrogenase (ldh), wherein said *E. coli* produces greater than 1 mole of succinate per mole of glucose under anaerobic culture conditions.

2. The engineered *E. coli* of claim 1, wherein said *E. coli* produces at least 1.3 mole of succinate per mole of glucose.

3. The engineered *E. coli* of claim 1, wherein said *E. coli* produces at least 1.4 mole of succinate per mole of glucose.

4. The engineered *E. coli* of claim 1, wherein said *E. coli* produces at least 1.5 mole of succinate per mole of glucose.

5. The engineered *E. coli* of claim 1, further comprising an inactivated *E. coli* gene encoding phosphotransferase G (ptsG).

6. The engineered *E. coli* of claim 5, wherein said *Escherichia coli* produces greater than 1.3 mole of succinate per mole of glucose.

7. The engineered *E. coli* of claim 1, further transformed with a DNA encoding phosphoenolpyruvate carboxylase (pepc).

8. The engineered *E. coli* of claim 1, further transformed with a DNA encoding formate dehydrogenase (fdh).

9. An engineered *E. coli*, comprising an inactivating deletion of all or part of the *E. coli* genes encoding alcohol dehydrogenase (adh) and lactate dehydrogenase (ldh) and a plasmid encoding pyruvate carboxylase (pyc), wherein said *E. coli* overexpresses pyc and produces greater than 1 mole of succinate per mole of glucose under anaerobic culture conditions.

10. The engineered *E. coli* of claim 9, further comprising an inactivating deletion of all or part of the *E. coli* gene encoding phosphotransferase G (ptsG).

11. The engineered *E. coli* of claim 9, which produces greater than 1.3 mole of succinate per mole of glucose.

12. The engineered *E. coli* of claim 10, which produces greater than 1.3 mole of succinate per mole of glucose.

13. The engineered *E. coli* of claim 10, which produces greater than 1.5 mole of succinate per mole of glucose.

14. The engineered *Escherichia coli* of claim 9, further transformed with a DNA encoding phosphoenolpyruvate carboxylase (pepc).

15. The engineered *Escherichia coli* of claim 6, further transformed with a DNA encoding formate dehydrogenase (fdh).

16. The engineered *E. coli* of claim 1, consisting essentially of:
   a) a DNA that expresses pyruvate carboxylase (pyc);
   b) inactivated *E. coli* genes encoding alcohol dehydrogenase (adh) and lactate dehydrogenase (ldh); and
   c) optionally one or more of an inactivated *E. coli* gene encoding phosphotransferase G (ptsG) or a DNA encoding phosphoenolpyruvate carboxylase (pepc) or a DNA encoding formate dehydrogenase (fdh), wherein said *E. coli* produces greater than 1 mole of succinate per mole of glucose under anaerobic culture conditions.

17. A method of producing succinate comprising culturing the *Escherichia coli* of any one of claim 1-15 or 16 under anaerobic conditions in the presence of glucose, and isolating succinate from said culture.

18. A method of producing succinate comprising:
   a) culturing the *Escherichia coli* of any one of claim 1-15 or 16 under aerobic conditions,
   b) transferring said *Escherichia coli* to anaerobic cultures with glucose, and
   c) culturing said *Escherichia coli* anaerobically to produce greater than 1 mole of succinate per mole of glucose.

* * * * *

UNITED STATES PATENT AND TRADEMARK OFFICE
CERTIFICATE OF CORRECTION

PATENT NO.         : 7,927,859 B2
APPLICATION NO.    : 10/923635
DATED              : April 19, 2011
INVENTOR(S)        : Ka-Yiu San, George N. Bennett and Ailen Sanchez Page 1 of 1

It is certified that error appears in the above-identified patent and that said Letters Patent is hereby corrected as shown below:

Column 1, under subtitle "FEDERALLY SPONSORED RESEARCH STATEMENT" line 12 substitute with the following paragraph:

This invention was made with government support under Grant Nos. BES-0000303 by the National Science Foundation. The government has certain rights in the invention.

Signed and Sealed this
Fifth Day of June, 2012

David J. Kappos
*Director of the United States Patent and Trademark Office*